(12) United States Patent
Foser

(10) Patent No.: US 6,371,762 B1
(45) Date of Patent: Apr. 16, 2002

(54) CERAMIC TOOTH RESTORATIONS AND METHOD FOR MANUFACTURING CERAMIC TOOTH RESTORATIONS

(75) Inventor: Hans-Peter Foser, Liechtenstein (DE)

(73) Assignee: Ivoclar AG, Liechtenstein ( * ) Notice: Subject to any disclaimer, the term of this patent is extended or adjusted under 35 U.S.C. 154(b) by 0 days.

(21) Appl. No.: 09/441,219

(22) Filed: Nov. 15, 1999

(30) Foreign Application Priority Data

Nov. 23, 1998 (DE) .......................... 198 53 949

(51) Int. Cl.⁷ ............................... A61C 13/003
(52) U.S. Cl. ................. 433/180; 433/181; 433/192
(58) Field of Search ..................... 433/180, 181, 433/182, 183, 191, 192, 193, 194, 195

(56) References Cited

U.S. PATENT DOCUMENTS 4,744,757 A    5/1988  Adair et al.
4,950,162 A  * 8/1990  Korber et al. .............. 433/180
5,074,791 A  * 12/1991 Shoher et al. .............. 433/180
5,788,498 A  * 8/1998  Wohlwend .................. 433/223
5,968,856 A  * 10/1999 Schweiger et al. ............ 501/7

FOREIGN PATENT DOCUMENTS

DE          197 50 794 A1    6/1999

* cited by examiner

Primary Examiner—Ralph A. Lewis
(74) Attorney, Agent, or Firm—John C. Thompson; Alan S. Korman

(57) ABSTRACT

A ceramic tooth restoration has two neighboring ceramic tooth replacement elements each having a recess. A connecting member is placed into the recesses. A glass paste is provided for anchoring the connecting member in the recesses by sintering at a temperature below approximately 800° C.

17 Claims, 1 Drawing Sheet

CERAMIC TOOTH RESTORATIONS AND METHOD FOR MANUFACTURING CERAMIC TOOTH RESTORATIONS

TECHNICAL FIELD

The present invention relates to a method for manufacturing ceramic tooth restorations comprising a connecting element which is inserted in recesses of two tooth replacement elements such as crowns or bridge members neighboring each other. The present invention also relates to a method for manufacturing such a ceramic tooth restoration.

BACKGROUND OF THE INVENTION

A tooth restoration of the aforementioned kind is known from U.S. Pat. No. 4,744,757. In this tooth restoration, a connecting element is inserted into recesses of two neighboring bridge members, as shown in FIG. 3 of the patent. It is still possible to move the tooth restoration before it is finally fixed in its position. For accomplishing this, a bonding agent or tooth cement is used which hardens after the solvents contained therein evaporate. Alternatively, light-curable resins can be used, in which case it is assumed that the ceramic materials used for the manufacture of tooth restorations are sufficiently light-penetrable in the spectrally important UV-range in order to ensure a secure light-curing result.

A disadvantage of this solution, however, is that the curing degree depends on the ceramic material used. For safety reasons, the tooth restoration should only be made out of a glass ceramic material that is especially easily penetrated by light.

The tooth restorations manufactured according to that method have proven to be not particularly durable. In particular, where dental cements have been used, cracks occurred which are perhaps traceable to non-compatible thermal extension coefficients.

In contrast thereto, it is an object of the present invention to create a tooth restoration comprising a connecting element which is inserted in recesses of two tooth replacement elements (crowns or bridge members) neighboring each other and a method for manufacturing such a tooth restoration so as to provide a long-term stable and reliable connection between crowns or bridge members without negatively affecting the free adjustability thereof.

OBJECTS AND SUMMARY OF THE INVENTION

This object is solved with the inventive ceramic tooth restoration by sintering the connecting element into the recesses at temperatures below approximately 800° C. by means of a glass powder paste or glass powder slurry.

Surprisingly, the inventive sintering process of the connecting elements by means of glass powder pastes or glass powder slurries (in the following the term glass paste will be used for both the glass powder paste and the glass powder slurry) results in a durable tooth restoration which especially is not prone to the formation of cracks. The glass materials used for the sintering process can be selected easily such that their thermal extension coefficients lie at least in the vicinity of those of the ceramic material used. When, for example, a lithium disilicate ceramic is used with a thermal extension coefficient of $10.8 \times 10^{-6}$/K, a lithium disilicate glass material can be used without a problem as a sintering material. By baking the connecting elements into the crowns or bridges, a particularly well reinforced connection is created. By selecting the baking temperature appropriately, it can be ensured that the ceramic material itself does not lose its hardness. Temperatures in the range of between 600° and 800° C. are preferred for the sintering process.

According to the current restoration technologies, full ceramic bridge reconstructions have to be manufactured anew if there are fitting problems because no adequate ceramic bonding technique exists. According to the present invention a repeated manufacture of the cost-intensive full-ceramic restoration becomes obsolete and, furthermore, it does not require any plastic patching.

According to a particularly favorable aspect of the invention, a stable and durable bridge can also be manufactured when the side walls of the tooth restoration are relatively thin. In this case the inventive connecting element is positioned in the area of the grinding surface and is practically inserted from above as a small plate and is fired subsequently. It is understood that the selection of the length and measurements of the connecting element can be adjusted to the requirements in a wide range.

Also, the shape and design of the connecting element can be largely adjusted to the requirements. In particular, if the connecting element extends in the area of the grinding surfaces, an oblong and flat design can offer an especially stable connection. Instead of pin-shaped connecting elements, bone-shaped connecting elements can also be inserted whereby in each case play or a spacing is provided between the recesses and the connecting element so that the glass paste can be received.

The recess oversize relative to the connecting elements can be largely adjusted as required. It is possible, for example, to provide a gap of, e.g. ¹/₁₀ of the thickness of the connecting element and entirely fill this gap with glass-sintering material.

The filling can be performed such that the recesses are filled with glass paste, or, preferably, by immersing the connecting elements in the glass paste and, subsequently, inserting them into the recesses of the crown or bridge members.

Subsequent to the insertion, the bridge or crown is introduced into the model or into the mouth of the patient and the correct positioning is defined. Subsequently, the geometry is stabilized by suitable mechanical procedures, e.g., by clamps, fixing gypsum, or plastic, and the thus prepared tooth restoration is post-sintered in a short firing process so that the connecting elements become securely anchored within the recesses and a connection of long term stability is ensured.

The object and advantages of the present invention will appear more clearly from the following specification in conjunction with the accompanying schematic drawings in which preferred embodiments of this invention are illustrated.

DETAILED DESCRIPTION

The present invention will now be described in detail with the aid of several specific embodiments utilizing FIGS. 1 through 4.

Figure 1:
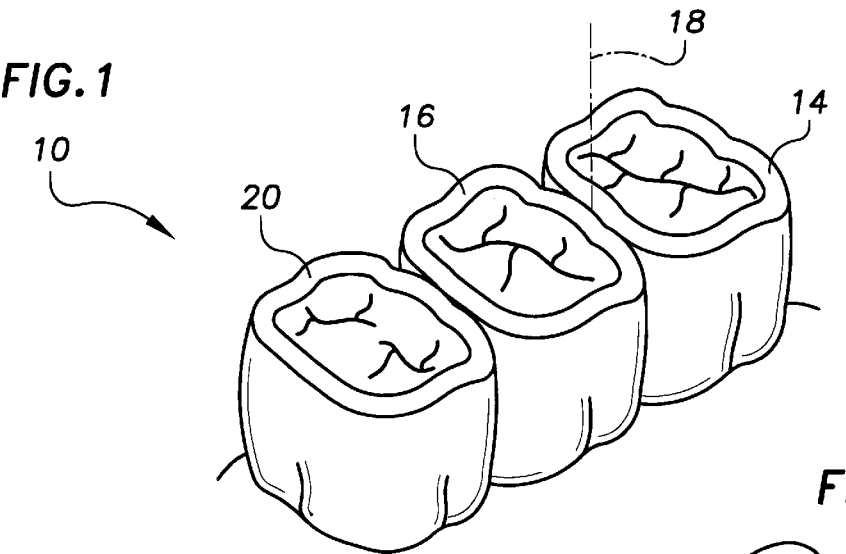
FIG. 1 shows a schematic perspective view of a bridge for use in the context of the inventive method.

The embodiment according to FIG. 1 shows a bridge 10 as a tooth restoration which is separated between a crown 14 and a bridge tooth 16 along, a separation line 18. However, the connection between the bridge tooth 16 and another crown 20 remains intact; for an optimum alignment it is sufficient to have only one separation per bridge.

In the herein described preferred embodiment, the bridge 10 is comprised of a lithium disilicate ceramic material with respect to which reference is made to the complete disclosure of DE-OS 197 50 794. The thermal extension coefficient of this ceramic material lies at $10.8 \times 10^{-6}$/K in the range of between 100° and 500° C.

Figure 2:
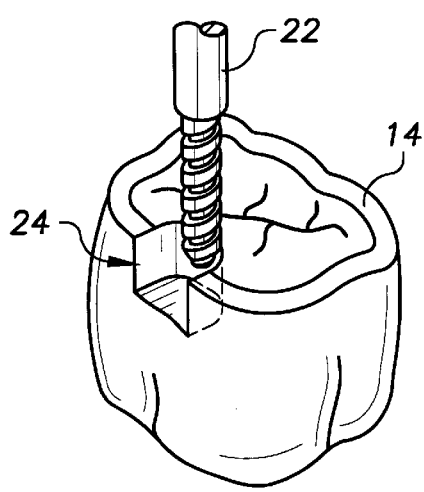
FIG. 2 shows a perspective view of a crown or a bridge member subsequent to its separation from the bridge according to FIG. 1.
Figure 3:
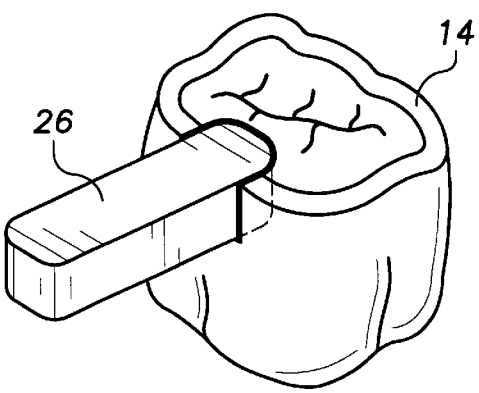
FIG. 3 shows a perspective view of the bridge member according to FIG. 2 with the connecting element being inserted on one side only.

Subsequent to the separation process, a recess 24 is created by means of a drill or milling device 22 (see FIG. 2). The recess 24 is slightly larger than the connecting element 26 shown in FIG. 3. A matching recess 24 is produced in the crown 14 as well as in the bridge tooth 16. In the shown embodiment, the recesses 24 extend in the medial/distal wall area of the crown.

For the connection a prepared fusing glass paste is use. In a preferred embodiment of the invention, a low fusing glass having a thermal expansion coefficient of 0.8 to $10 \times 10^{-6}$/K is ground at 100° to 500° C. This glass has a sinter range between 640° and 740° C. and the particles size to be achieved by grinding is smaller than 100 Nm. The glass substance is mixed with a solvent of low volatility. Polyethylene glycol 425 or ethylene glycol are especially suitable for this.

As a connecting member 26 a pin of a rigid material such as $ZrO_2$ is preferably used. The pin is preferably premanufactured or is cut or broken off to the desired length.

Before insertion of the tooth restoration into the mouth of the patient or into the model, the prepared glass paste is pasted onto the connecting member 26 and the connecting member 26 is placed into the prepared recesses 24 so that the excess glass paste flows out. The excess is removed, and proper fitting is performed.

As soon as the proper fitting has been found, the geometry of the bridge is additionally stabilized. Even though the glass paste is relatively viscous, so that a certain force is required for changing the alignment of the tooth replacement elements relative to one another, it is favorable and beneficial when a geometric reinforcement, for example, by a suitable clamp or fusing material is provided.

The aligned and fixated bridge 10 is then again removed and introduced into the ceramic firing furnace together with the connecting member 26. For example, a furnace of the model "Programat", a device produced by the assignee of the present invention, can be used.

Within 30 minutes the temperature of the furnace is increased to 690° C. and held at that temperature for one minute. Within 10 minutes the furnace is then cooled to room temperature.

It is preferred that the employed glass paste has a sinter point that is considerable above the sinter point of the ceramic material of the tooth replacement element but still has a thermal expansion coefficient in the range of the thermal expansion coefficient of the ceramic.

Figure 4:
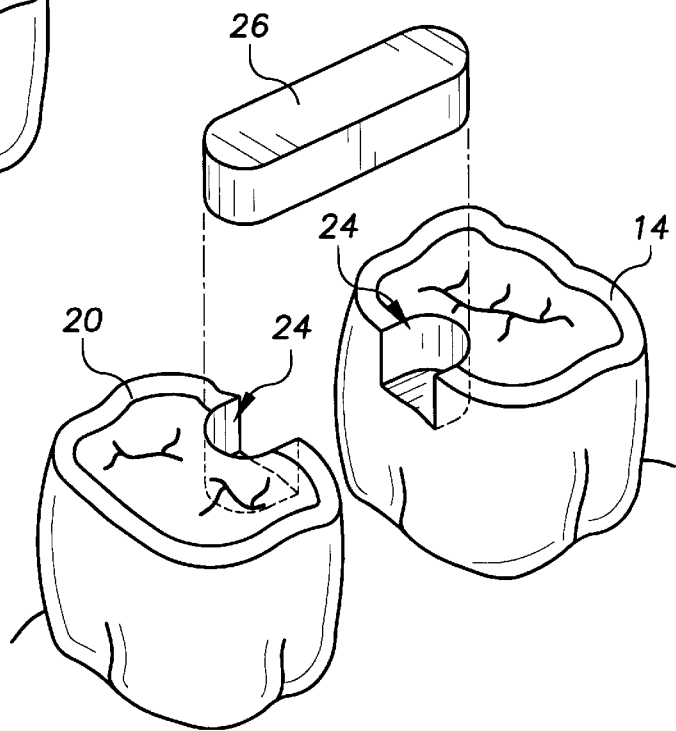
FIG. 4 shows a further design of an inventive tooth restoration with a modified design of the connecting element.

FIG. 4 shows a further embodiment of the inventive tooth restoration 12. A crown 20 is connected by a connecting member 26 to a crown 14. In this embodiment the connecting member 26 is positioned in the area of the grinding surface of the tooth. The recesses 24 have a shape that is configured similarly to the shape of the connecting member 26 but are somewhat larger. In this embodiment, the connecting member may be inserted into the recesses 24 after the crowns 14 and 20 have already been aligned to one another in the mouth of the patient or in the model. It is preferred to cover the grinding surface subsequently with a further cover layer, while sintering can be performed as disclosed above.

According to an alternative embodiment, a conventional fusing material is used, for example, the product INSTA-FRAC produced by company Ceramic Work, instead of the glass paste.

In both cases, the results after the final sintering are satisfactory.

It is understood that the embodiment can be adjusted in wide ranges to the respective requirements. For example, instead of the connecting member with rounded ends, it is possible to adapt the shape and cross-section of the connecting member 26 to the load situation. In this context it is recommended to employ an elliptical cross-section having a longitudinal axis extending in the incisal/gingival direction Inventively, it is also beneficial when the material for the connecting member 26 is zirconium dioxide. This material is even harder than a lithium disilicate ceramic so that a stiffening of the bridge can be realized with the inventive connecting member.

According to a final embodiment, it is suggested to embody the connecting member longer and bigger so that it extends through the bridge tooth, but is still sintered with a glass paste into the respective recesses.

The present invention is, of course, in no way restricted to the specific disclosure of the specification and drawings, but also encompasses any modifications within the scope of the appended claims.

What is claimed is:

1. A ceramic tooth restoration comprising:
   two neighboring tooth replacement elements (14, 20) formed of a ceramic material, each one of said tooth replacement elements having a recess (24);
   a connecting member (26) placed into said recesses (24); and
   a glass paste for sintering said connecting member (26) into said recesses (24) at a temperature below approximately 800° C., said glass paste having a thermal expansion coefficient which is close to a thermal expansion coefficient of the ceramic material of said tooth replacement elements (14, 16, 20).

2. A ceramic tooth restoration according to claim 1, wherein said recesses (24) are embodied in neighboring medial or distal sides of said tooth replacement elements (14, 16, 20).

3. A ceramic tooth restoration according to claim 2, wherein said recesses (24) penetrate said medial or distal sides of said tooth replacement elements (14, 16).

4. A ceramic tooth restoration according to claim 1, wherein said recesses (24) are positioned in neighboring grinding surfaces of said tooth replacement elements (14, 16, 20) and extend over at least 20% and at most half of a medial or distal length of said tooth replacement elements (14, 16, 20).

5. A ceramic tooth restoration according to claim 1, wherein said connecting member (26) is a pin having a rectangular, cylindrical, or oval cross-section and wherein said recesses (24) have a cross-section configured to match said cross-section of said connecting member (26).

6. A ceramic tooth restoration according to claim 1, wherein said cross-section of said recesses (24) is larger than said cross-section of said connecting member (26) and wherein said tooth replacement elements (14, 16, 20), when said connecting member (26) is inserted into said recesses (24), are movable by a limited amount before said glass paste is sintered.

7. A ceramic tooth restoration according to claim 6, wherein a difference between said cross-section of said recesses (24) and said connecting member (26) is substantially identical at a buccal, labial, gingival, and, optionally, incisal side of said connecting member (26).

8. A ceramic tooth restoration according to claim 7, wherein said difference is between 3% to 30% of a diameter of said connecting member (26).

9. A ceramic tooth restoration according to claim 8, wherein said difference is 10% of said diameter of said connecting member (26).

10. A ceramic tooth restoration according to claim 1, wherein said recesses (24) are produced by grinding or cutting.

11. A ceramic tooth restoration according to claim 1, wherein said glass paste is applied to said connecting member (26) before said connecting member (26) is inserted into said recesses (24).

12. A ceramic tooth restoration according to claim 1, wherein said glass paste contains feldspar glass or a lithium disilicate glass and wherein said connecting member (26) is comprised of one or more metal oxides, wherein said metal oxide is selected from the group consisting of $SiO_2$, $Al_2O_3$, and $ZrO_2$.

13. A method for preparing a ceramic tooth restoration, said method comprising the steps of:

preparing recesses (24) in neighboring tooth replacement elements formed of a ceramic material (14, 16, 20);

inserting a connecting member (26) into said recesses (24);

filling a space remaining between an outer surface of said connecting member (26) and inner surfaces of said recesses (24) with a glass paste, said glass paste having a thermal expansion coefficient which is close to a thermal expansion coefficient of the ceramic material of said tooth replacement elements (14, 16, 20);

heating said tooth restoration to melt said glass paste; and cooling said tooth restoration to harden said glass paste and thereby fixedly and rigidly connecting said connecting member (26) in said recesses (24).

14. The method according to claim 13, wherein said step of heating is carried out for less than 3 minutes and wherein the temperature during said step of heating is less than 800° C.

15. The method according to claim 14, wherein said step of heating is carried out for approximately 1 minute and wherein the temperature during said step of heating is 640° to 740° C.

16. The method according to claim 14, wherein the correct position of said tooth replacement elements (14, 16, 20) are determined by placing the tooth replacement elements (14, 16, 20) with said inserted connecting member (26) into a patient's mouth, the tooth replacement parts being fixed in the correct position.

17. The method according to claim 14, wherein the correct position of said tooth replacement elements (14, 16, 20) are determined by placing the tooth replacement elements (14, 16, 20) with said inserted connecting member (26) into a model, the tooth replacement parts being fixed in the correct position.

* * * * *